(12) United States Patent  (10) Patent No.: US 8,480,610 B1
Hill  (45) Date of Patent: Jul. 9, 2013

(54) EAR TUBE AND METHOD OF INSERTION

(76) Inventor: Frank C. Hill, Columbia, SC (US)

( * ) Notice: Subject to any disclaimer, the term of this patent is extended or adjusted under 35 U.S.C. 154(b) by 1985 days.

(21) Appl. No.: 11/157,513

(22) Filed: Jun. 21, 2005

Related U.S. Application Data

(63) Continuation-in-part of application No. 10/197,977, filed on Jul. 18, 2002, now abandoned, which is a continuation-in-part of application No. 09/452,863, filed on Dec. 8, 1999, now abandoned.

(60) Provisional application No. 60/111,492, filed on Dec. 8, 1998.

(51) Int. Cl.
*A61M 5/00* (2006.01)

(52) U.S. Cl.
USPC .............................................................. 604/8

(58) Field of Classification Search
USPC ........................ 604/8, 9, 264; 606/109; 623/10
See application file for complete search history.

(56) References Cited

U.S. PATENT DOCUMENTS

| | | | |
|---|---|---|---|
| 3,062,211 A | 11/1962 | Walden et al. | |
| 3,717,151 A | 2/1973 | Collett | |
| 3,871,380 A | 3/1975 | Heros | |
| 3,948,271 A | 4/1976 | Akiyama | |
| 4,043,346 A | 8/1977 | Mobley et al. | |
| 4,175,563 A * | 11/1979 | Arenberg et al. | 604/9 |
| 4,764,168 A | 8/1988 | Sub | |
| 4,808,171 A | 2/1989 | Berger | |
| 4,986,810 A | 1/1991 | Semrad | |
| 5,116,327 A | 5/1992 | Seder et al. | |
| 5,139,502 A | 8/1992 | Berg et al. | |
| 5,176,626 A * | 1/1993 | Soehendra | 604/8 |
| 5,178,623 A | 1/1993 | Cinburg et al. | |
| 5,207,685 A | 5/1993 | Cinburg et al. | |
| 5,254,120 A | 10/1993 | Cinberg et al. | |
| 5,273,527 A | 12/1993 | Schatz et al. | |
| 5,273,534 A | 12/1993 | Knoepfler | |
| 5,649,932 A | 7/1997 | Fouin et al. | |
| 5,702,414 A | 12/1997 | Richter et al. | |
| 5,711,309 A | 1/1998 | Goldenburg | |
| 5,795,288 A | 8/1998 | Cohen et al. | |
| 5,817,062 A | 10/1998 | Flom et al. | |
| 5,868,699 A | 2/1999 | Woodruff et al. | |
| 6,099,506 A | 8/2000 | Macoviak et al. | |
| 6,406,453 B1 * | 6/2002 | Goode et al. | 604/8 |

OTHER PUBLICATIONS

Bulkley WJ, Bowes AK, and Marlowe JF. "Complications Following Ventilation of the Middle Ear Using Goode T-Tubes." Arch Otolawngol Head Neck Surgery, vol. 117, Aug. 1991.*
Kay DJ, Nelson M, and Rosenfeldd RM. "Meta-Analysis of Typanostomy tube sequelae." Otolaryngol Head Neck Surgery, 2001:124:374-80.*
Hill, F. "The Triune, a New Silicone Tympanostomy Tube." Otolaryngology-Head and Neck Surgery, (2006) 134, 524-525.*

* cited by examiner

*Primary Examiner* — Leslie Deak
(74) *Attorney, Agent, or Firm* — Gordon & Jacobson, PC

(57) ABSTRACT

An ear tube for draining and ventilating the middle ear that prevents perforation of the ear drum. The tube comprises a tubular stem having a lumen formed in it and a pair of ports formed in its walls for providing access to the lumen from the sides. A plurality of resilient arms extend from one end of stem at an angle to the stem and each other. Once through the membrane, the arms resiliently spring open to anchor the tube.

13 Claims, 2 Drawing Sheets

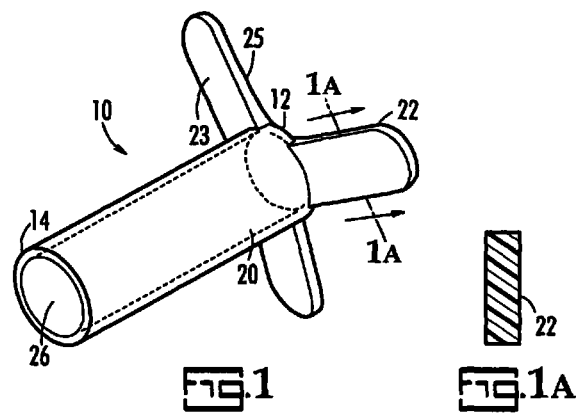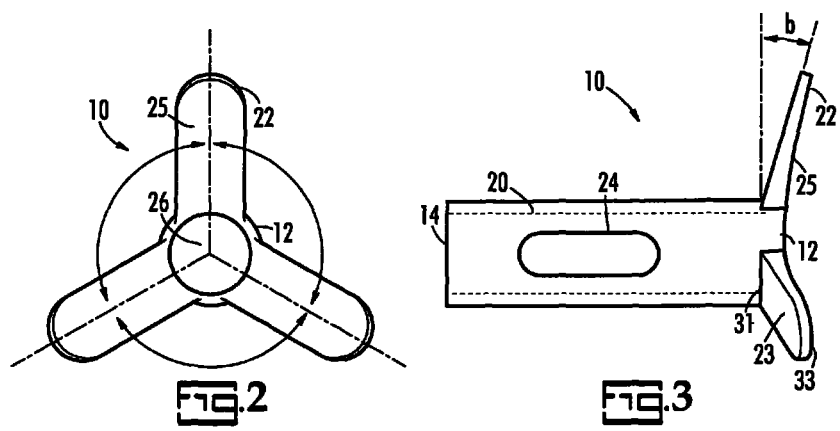

EAR TUBE AND METHOD OF INSERTION

CROSS REFERENCE TO RELATED APPLICATIONS

This application claims the benefit of U.S. Provisional Application No. 60/111,492, filed Dec. 8, 1998, and is a continuation-in-part of nonprovisional U.S. application Ser. No. 10/197,977 filed Jul. 18, 2002, now abandoned which was a continuation-in-part of U.S. application Ser. No. 09/452,863 filed Dec. 8, 1999, now abandoned the entire contents of these prior applications being expressly incorporated herein by reference.

STATEMENT REGARDING FEDERALLY SPONSORED RESEARCH OR DEVELOPMENT

Not applicable.

REFERENCE TO A SEQUENCE LISTING, A TABLE, OR A COMPUTER PROGRAM LISTING COMPACT DISK APPENDIX

Not applicable.

BACKGROUND OF THE INVENTION

The present invention relates to ear tubes. In particular, the present invention relates to tubes for draining fluid through the eardrum and methods of inserting the tubes.

Typically, pressure within the middle ear is regulated by the Eustachian tube. Whenever the pressure within the middle ear is greater or less than the surrounding atmosphere, the Eustachian tube opens to equalize pressure. If the Eustachian tube is not functioning properly, the pressure within the middle ear tends to drop. The negative pressure in the middle ear draws fluid from the surrounding tissue and causes fluid to accumulate in the middle ear. This fluid causes swelling and infections within the middle ear.

In order to drain and ventilate the middle ear, ear tubes can be used. The tubes equalize pressure with the surrounding atmosphere, thereby eliminating the accumulation of fluid and reducing the risk of infection. To install a tube, a small incision is cut in the tympanic membrane, commonly called the ear drum, and the tube is inserted through the incision.

There are various types of ear tubes. One type of tube is formed as a shank with a trailing flange. This type of tube tends to fall out of the ear after a short period of time. Another type of tube, commonly called a T-tube on account of its shape, rarely falls out spontaneously, but requires removal by a physician. The T-tube has a flange that resiliently opens upon insertion through the ear drum, much like a toggle bolt. Unfortunately, the T-tube suffers from several disadvantages. The T-tube tends to leave a perforation in the eardrum about 25% of the time, which is considerably more than other types of tubes. The flange of the T-tube unfolds at an angle of 90° to the axis of the tube. These arms tend to "tent up" the eardrum and erode through the ear drum, causing a perforation. The reason for this "tenting-up" is that the eardrum is not flat, as sometimes thought, but has a complex curved shape such that the shape of a conventional T-tube puts undo pressure on the eardrum. Moreover, the T-tubes tend to shift and align themselves across the ear canal or block the tube, thereby making it difficult to see down the lumen of the tube to determine if the tube is obstructed. Additionally, the T-tubes tend to become obstructed with a plug of desiccated fluid or blood.

Yet another disadvantage of these T-tubes is the need for special instruments for inserting the tubes. During the insertion of the T-tubes, instruments are required to keep the arms of the T-tubes in alignment before the tube is pushed through the tympanic membrane. The insertion instruments are often difficult to operate and can cause the overall draining process to be both lengthy and tedious.

Therefore, there is a need for an improved ear tube that can be inserted without the use of special instruments and that stays in place unless removed, but does not tend to cause permanent perforations in the ear drum and that stays perpendicular to the ear drum and that can be readily cleared if it becomes obstructed.

SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention. Its sole purpose is to present some concepts of the invention in a simplified form as a prelude to the more detailed description that is presented later.

According to its major aspects and broadly stated, the present invention is an ear tube for draining and ventilating the middle ear and method of insertion. The ear tube includes a cylindrical stem having a lumen longitudinally formed therein. A plurality of arms, preferably more than two, extend from one end of the stem. These arms can be folded back on the stem to fit within a cut into the tympanic membrane, and then resiliently spring back into place once through the tympanic membrane to anchor the tube. The arms are preferably angled down from perpendicular about 10° to about 40° when open based on the longitudinal axis of the stem. Furthermore, the arms are preferably flat with a smooth surface. The arms can additionally be reinforced at the attachment points of the arms with the stem. The stem can be made from a translucent material so that one can see if it is plugged, while the arms can be formed from a colored, opaque material so that a physician could easily see the arms through the translucent tympanic membrane. Furthermore, the stem can have a port extending through the surface of the stem for providing access to the lumen.

The present invention further includes a method for inserting the ear tube. The method includes the following steps: 1) providing an ear tube having a stem and angled arms extending radially from one end of the stem; 2) grasping the stem with means for grasping; 3) pushing the arms of the ear tube through the tympanic membrane; and 4) disengaging grasping means from the stem.

A feature of the present invention is the use of an ear tube having a stem with more than two arms that extend radially from the end of the stem. Standard ear tubes include stems having two arms. The use of a third arm or more facilitates the alignment of the ear tube with the tympanic membrane. Further, the additional arm or arms prevents premature extrusion of the ear tube from the tympanic membrane. Accordingly, the number of arms contributes to the stability of the ear tube within the tympanic membrane.

Another feature of the present invention is the use of an ear tube having flat arms. The arms of most ear tubes are semi-circular in cross section. This shape is not an ideal complement to the shape of the eardrum. According, using flat arms allows for better anchoring of the ear tube and minimizes potential abrasion of the eardrum once the tube is inserted.

Still another feature of the present invention is the use of an ear tube having angled arms. The arms of the present invention can be angled about 10° to about 40° down from a perpendicular plane in relation to the stem of the arm. Preferably, the angle is about 15° down from a perpendicular plane in relation to the longitudinal axis of the stem. This angle enables the tube to conform to the anatomy of the tympanic membrane, which is curved. The ear tube is therefore able to anchor itself to the eardrum is minimal disruption to the surface of the eardrum. Consequently, the incidence of perforations in the tympanic membrane is greatly reduced.

Yet another feature of the present invention is the use of an ear tube that is smooth. In particular, the ear tube can be made of silicone that is extruded through cold extrusion rather than hot extrusion. Cold extrusion is a standard practice known in the art wherein materials are extruded at room temperature or slightly elevated temperatures. The use of this process allows the ear tube to have a smoother texture than if hot extrusion is used. Because the eardrum is constantly vibrating, a tube that is soft, and conforms to the eardrum is less likely to traumatize the eardrum. Because of the features of the ear tube of the present invention, the ear tube can actually move with the eardrum upon insertion as the eardrum is vibrating. Other types of ear tubes that are stiffer actually move against the eardrum surface with its movement.

Still another feature of the present invention includes the use of an ear tube having arms that are reinforced at the attachment point of the arms with the stem of the ear tube. The use of reinforcement to the arms facilitates the folding of the arms back onto the stem when the ear tube is being inserted. Furthermore, after the ear tube is inserted, the reinforcement makes the ear tube more resistant to bending forward, which can determine how long the ear tube stays in place.

Another feature of the present invention includes the optical characteristics of the ear tube. Both the stem and the collar are made from a translucent material. As a result of this feature, the physician can more easily detect any obstructions clogging the lumen of the tube. Further, the physician can view the positioning of the arms as they are being pushed through the collar and into the tympanic membrane. Additionally, the arms of the ear tube are made of an opaque material so that they can be detected through the tympanic membrane. This feature allows for easier installation of the tube since the physician can detect the positioning of the arms through the tympanic membrane.

The arm configuration that withstands rotation or shifting within the tympanic membrane is another important feature of the present invention. Consequently, the tube will not be blocked by becoming mispositioned with the end against the ear canal. The physician can look down the lumen or through the translucent wall of the tube to detect any obstructions.

The ability to clear any obstructions from the tube in situ is an important advantage of the present invention. This advantage is enabled by the ports formed in the stem of the tube, which allow a physician easy access to remove any desiccated plug or blood clot by grasping it through the ports, without requiring removal or replacement of the tube.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

FIG. 1 is a perspective view of an ear tube according to a first preferred embodiment of the present invention;

FIG. 1A is a cross sectional view taken from line 1A of an arm of the ear tube according to a first preferred embodiment of the present invention;

FIG. 2 is a front view of the ear tube according to the first preferred embodiment of the present invention;

FIG. 3 is a side view of the ear tube according to a second preferred embodiment of the present invention.

DETAILED DESCRIPTION OF A PREFERRED EMBODIMENT

Figure 4A:
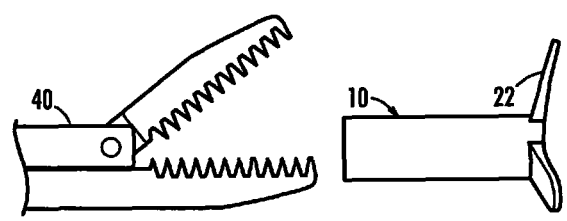
FIG. 4A is a side view of the ear tube and an insertion device according to the first preferred embodiment of the present invention.

Referring now to the figures, the present invention is an ear tube for draining and ventilating the middle ear. As shown in FIGS. 1-3, the tube, generally referred to by reference number 10, includes a tubular stem 20 having a lumen 26 longitudinally formed therein from end of the stem 20 to the other end of the stem 20. By the term lumen, it is meant an interior space of tubular stem 20. For purposes of orientation in referring to the drawings, tube 10 has a front end 12 and a rear end 14. The stem 20 is preferably cylindrical in shape having sufficient dimensions to fit within an incision in the tympanic membrane of a human ear. Further, the lumen 26 is of sufficient diameter to provide drainage and ventilation from the middle ear to the outer ear, and preferably has a diameter similar to that of ear tubes in use in the art. Alternatively, the stem 20 can include at least one port 24 formed in the wall of the stem 20 for providing access to the lumen 26. If included, the port 24 extends laterally therethrough, that is, perpendicular to the axis of stem 20. The port 24 can be of sufficient area to allow a physician access to any obstruction that may be blocking lumen 26 of the tube 10 in situ.

A plurality of arms 22 extend from the front end 12 of stem 20. Preferably, the plurality of arms 22 includes more than two arms. These arms can be spaced apart equidistant from each other. As discussed, the use of a third arm or more facilitates the alignment of the ear tube 10 with the tympanic membrane. Further, the additional arm or arms prevents premature extrusion of the ear tube 10 from the tympanic membrane. Accordingly, the number of arms contributes to the stability of the ear tube 10 within the tympanic membrane.

In addition to the number of arms used in the ear tube 10, the structure of the ear tube 10 arms is a significant feature of the present invention. As illustrated, each arm of the plurality of arms 22 includes an attachment point 31 with the stem 20 and an end point 33. Preferably, each arm of the plurality of arms is flat in cross section, as shown in FIG. 1A. A particular feature of the present invention includes the use of flat arms. The arms of most ear tubes are semicircular in cross section. This shape is not an ideal complement to the shape of the eardrum. Accordingly, using flat arms allows for better anchoring of the ear tube 10 and minimizes potential abrasion of the eardrum once the tube 10 is inserted.

Each arm of the plurality of arms 22 can further include a form of reinforcement at the attachment point 31 of the arms with the stem 20. For example, the arms can be beveled so that the arms are thicker at the attachment point 31 than the end point 33 of each arm. As previously discussed, the use of arms that are reinforced at the attachment point 31 of the arms with the stem 20 of the ear tube 10 is a particular feature of the present invention. The use of reinforcement to the arms facilitates the folding of the arms back onto the stem 20 when the ear tube 10 is being inserted. Furthermore, after the ear tube 10 is inserted, the reinforcement makes the ear tube 10 more resistant to bending forward, which can determine how long the ear tube 10 stays in place.

Additionally, each arm of the plurality of arms 22 is preferably angled to such a degree that best complements the natural curvature of the tympanic membrane. The arms of the present invention can be angled about 10° to about 40° down from a perpendicular plane in relation to the longitudinal axis of the stem 20 of the ear tube 10. Preferably, the angle is about 15° down from a perpendicular plane in relation to the longitudinal axis of the stem 20, which is shown as angle b in FIG. 3. This angle enables the ear tube 10 to conform to the anatomy of the tympanic membrane. The ear tube 10 is therefore able to anchor itself to the eardrum with minimal disruption to the surface of the eardrum. Consequently, the incidence of perforations in the tympanic membrane is greatly reduced.

The ear tube 10 of the present invention is preferably made of a smooth material. In particular, the ear tube 10 can be made of extruded silicone has a hardness of about 70 durometers. Further, the silicone can be extruded through the use of cold extrusion rather than hot extrusion. As discussed, cold extrusion is a standard practice known in the art wherein materials are extruded at room temperature or slightly elevated temperatures. The use of this process allows the ear tube to have a smoother texture than if hot extrusion is used. Because the eardrum is constantly vibrating, a tube that is soft and pliable is less likely to traumatize the eardrum. Because of the features of the ear tube 10 of the present invention, the ear tube 10 can actually move with the eardrum upon insertion as the eardrum is vibrating. Other types of ear tubes that are stiffer have greater potential to move against the eardrum surface with the eardrum movement.

Alternatively, the ear tube 10 can include various optical characteristics that can enhance the performance of the ear tube 10. However, these optical characteristics are not necessary to the present invention. If included, the stem 20 can be formed from a translucent material. This translucent material in conjunction with a port 24 can allow a physician easy access to detect and remove any obstructions blocking lumen 26 without removing or replacing tube 10. In addition, the arms of ear tube 10 can be made of a colored or opaque material so that the positioning of the arms can be viewed once the arms have been inserted within the tympanic membrane, which is more translucent than the opaque or colored material.

Figure 4B:
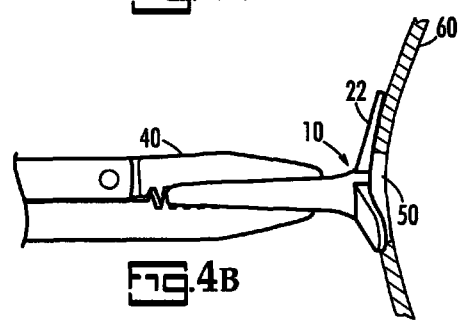
FIG. 4B is a side view of the ear tube being installed within the tympanic membrane with the insertion device according to the first preferred embodiment of the present invention.
Figure 4C:
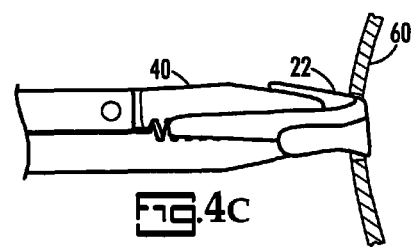
FIG. 4C is a side view of the ear tube being installed within the tympanic membrane with the insertion device according to the first preferred embodiment of the present invention.
Figure 4D:
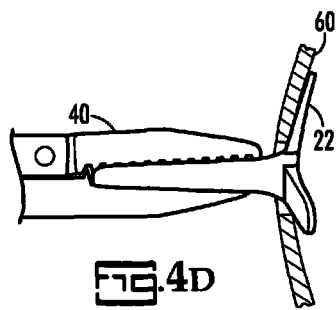
FIG. 4D is a side view of the ear tube being installed within the tympanic membrane with the insertion device according to the first preferred embodiment of the present invention.
Figure 4E:
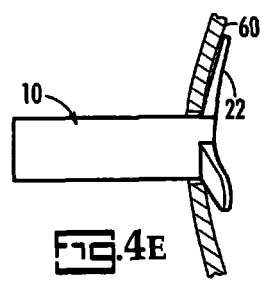
FIG. 4E is a side view of the ear tube installed within the tympanic membrane according to the first preferred embodiment of the present invention.

FIGS. 4A-4E illustrate the insertion or installation of the ear tube 10 of the present invention. In use, the ear tube 10 can be engaged by means for installing, such as a pair of alligator forceps 40 as shown. The installing means can clasp the stem 20 of the ear tube 10 and then force the arms of the ear tube 10 through an incision 50 made in the tympanic membrane 60. As illustrated, the arms have sufficient flexibility to fold back onto the stem 20 as the tube 10 is being inserted within the incision 50. Once the arms have passed through the incision 50, the arms resiliently open to anchor tube 10 from prematurely exiting from tympanic membrane 60. As further shown, the features of the ear tube 10, such as the use of angled, flat arms, enable the ear tube 10 to conform to the anatomy of the tympanic membrane 60. The lumen 26 in tube 10 equalizes pressure in the middle ear with that of the surrounding atmosphere; moreover, lumen 26 provides draining and ventilation of the middle ear in order to prevent further infection. Moreover, if the ear tube 10 includes the use of optical characteristics and the port 24, these features enable potential obstructions within the lumen 26 of the tube 10, such as blood or desiccated fluid clogging lumen 26 through the draining process, to be more easily removed.

It will be apparent to those skilled in the art that many changes and substitutions can be made to the preferred embodiments herein described without departing from the spirit and scope of the present invention

What is claimed is:

1. An ear tube for draining and ventilating a tympanic membrane, said tube comprising:
a stem having a first end and an opposing second end, said first end having a lumen formed therein between said first end and said second end;
at least three arms attached to said first end so that said at least three arms extend radially, each of said at least three arms including an attachment point and an end point, wherein each of said at least three arms are flat in cross section, wherein said at least three arms are angled to compliment the natural curvature of the tympanic membrane, and wherein each of said at least three arms are reinforced at said attachment point.

2. The ear tube as recited in claim 1, wherein said at least three arms are equally spaced about said first end of said stem.

3. The ear tube as recited in claim 1, wherein said at least three arms extend resiliently.

4. The ear tube as recited in claim 1, wherein said stem has at least one port extending therethrough between said first end and said second end.

5. The ear tube as recited in claim 1, wherein said stem and said at least three arms are made of extruded silicone.

6. The ear tube as recited in claim 5, wherein said extruded silicone has a hardness of about 70 durometers.

7. The ear tube as recited in claim 5, wherein said stem and said at least three arms are smooth.

8. The ear tube as recited in claim 1, wherein said at least three arms are angled about 10° to about 40° down from a perpendicular plane in relation to the longitudinal axis of said stem.

9. The ear tube as recited in claim 1, wherein said at least three arms are angled about 15° down from a perpendicular plane in relation to the longitudinal axis of said stem.

10. The ear tube as recited in claim 1, wherein said at least three arms are beveled.

11. The ear tube as recited in claim 1, wherein each arm of said at least three arms are thicker at said attachment point than said end point.

12. The ear tube as recited in claim 1, wherein said stem is made of a translucent material.

13. The ear tube as recited in claim 1, wherein said at least three arms are made of an opaque material.

* * * * *